(12) United States Patent
Schon et al.

(10) Patent No.: US 6,368,357 B1
(45) Date of Patent: Apr. 9, 2002

(54) THERAPEUTIC DEVICE FOR AMPUTEES

(75) Inventors: Lew Charles Schon, Baltimore, MD (US); John Rheinstein, New York, NY (US); Gregory Joseph Kowalcyzk, Hoboken, NJ (US)

(73) Assignee: Aircast, Inc., Summit, NJ (US)

( * ) Notice: Subject to any disclaimer, the term of this patent is extended or adjusted under 35 U.S.C. 154(b) by 0 days.

(21) Appl. No.: 09/174,498

(22) Filed: Oct. 16, 1998

(51) Int. Cl.$^7$ ............................. A61F 2/80; A61H 19/00
(52) U.S. Cl. .......................................... 623/37; 601/152
(58) Field of Search ............................. 623/37, 36, 33, 623/32; 602/62, 63; 601/151, 152

(56) References Cited

U.S. PATENT DOCUMENTS

| | | | |
|---|---|---|---|
| 1,057,562 A | 4/1913 | LaPoint | |
| 1,893,853 A | 1/1933 | Tullis | |
| 2,634,424 A | 4/1953 | O'Gorman | |
| 3,393,407 A | 7/1968 | Kandel | |
| 3,561,435 A | 2/1971 | Nicholson | |
| 3,671,980 A | 6/1972 | Baird | |
| 3,863,274 A | 2/1975 | Glabiszewski | |
| 3,889,301 A | 6/1975 | Bonner, Sr. | |
| 4,161,042 A | 7/1979 | Cottingham et al. | |
| 4,300,245 A | 11/1981 | Saunders | |
| 4,432,101 A | 2/1984 | Johnson | |
| 4,459,709 A | 7/1984 | Leal et al. | |
| 4,655,779 A | 4/1987 | Janowiak | |
| 4,840,635 A | 6/1989 | Smith et al. | |
| 4,842,608 A | 6/1989 | Marx et al. | |
| 4,923,475 A | 5/1990 | Gosthnian et al. | |
| 4,969,911 A | 11/1990 | Greene | |
| 5,108,456 A | * 4/1992 | Coonan et al. | 623/37 |
| 5,133,776 A | * 7/1992 | Crowder | 623/37 |
| 5,201,774 A | 4/1993 | Greene | |
| 5,314,496 A | 5/1994 | Harris et al. | |
| 5,441,533 A | 8/1995 | Johnson et al. | |
| 5,466,250 A | 11/1995 | Johnson, Jr. et al. | |
| 5,529,576 A | 6/1996 | Lundt et al. | |
| 5,571,209 A | 11/1996 | Brown, Sr. | |
| 5,577,998 A | 11/1996 | Johnson, Jr. et al. | |
| 5,588,955 A | * 12/1996 | Johnson, Jr. et al. | 601/152 |
| 5,651,792 A | * 7/1997 | Telikicherla | 623/36 |
| 5,653,766 A | * 8/1997 | Naser | 623/33 |
| 5,724,714 A | * 3/1998 | Love | 29/458 |
| 5,728,165 A | * 3/1998 | Brown, Sr. | 623/33 |
| 5,735,906 A | * 4/1998 | Caspers | 623/34 |
| 6,077,300 A | * 6/2000 | Sabolich et al. | 623/37 |

FOREIGN PATENT DOCUMENTS

EP          019612       5/1980

OTHER PUBLICATIONS

Atlas of Limb Prosthetics, 2d Edition, pps. 601–602, 620–622.

"Removable Rigid Dressing for Below–Knee Amputees," Clinical Prosthetics and Orthotics, vol. 11, No. 1, pps. 33–44, 1987.

(List continued on next page.)

Primary Examiner—David H. Willse
Assistant Examiner—Alvin Stewart
(74) Attorney, Agent, or Firm—Jones, Day, Reavis & Pogue

(57) ABSTRACT

A device is provided for applying therapeutic pneumatic pressure to the residual limb of an amputee in the post-operative stage. The device is intended for use in the immediate post-operative phase, i.e., immediately after surgical amputation of a limb. The device is intended to promote healing and proper residual limb formation after surgery. The device may comprise a calm-shell-like outer shell, the halves of which are joined together by a fastening means. A two-piece outer shell construction may also be used. The interior of the outer shell is fitted with inflatable bladders which, in combination, encompass the circumferential surface of the residual limb. An additional bladder may be provided at the distal end of the outer shell to cover the lower-most portion of the residual limb. The pressure within each bladder may be varied and adjusted.

19 Claims, 3 Drawing Sheets

OTHER PUBLICATIONS

"Management of Lower Extremity Amputations," Burgess, Romano, Zettl, Chapter 6, Postoperative Management, Jul. 3, 1997.

Flo–Tech Orthotic and Prosthetic Systems product literature, 2 pages.

U.S. Mfg. Co. Lightweight Adjustable Sockets—Pneu–Fit product literature, 2 pages.

Otto Bock Interim Prostheses/Saarbrucken Early Fitting Prostheses product literature, 2 pages.

Knit–Rite, Inc., O & P Distributors, Prosthetic Supplies product literature, pps. 238, 246.

Direct Fit & Adjustable BK Sockets product literature, 1 page.

* cited by examiner-

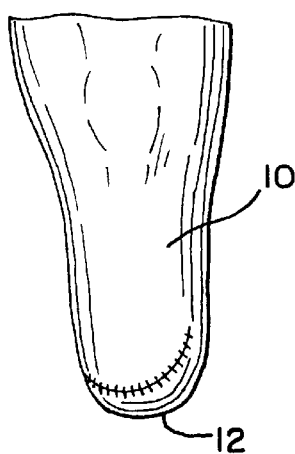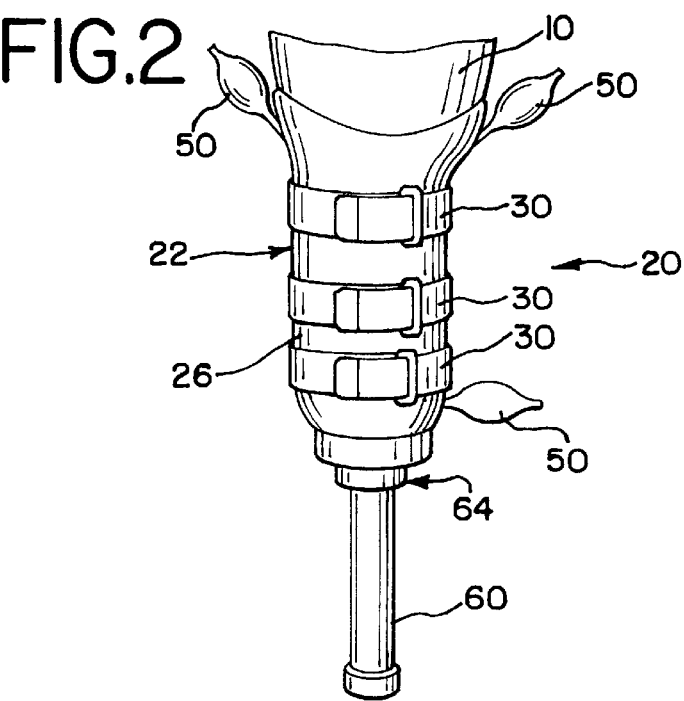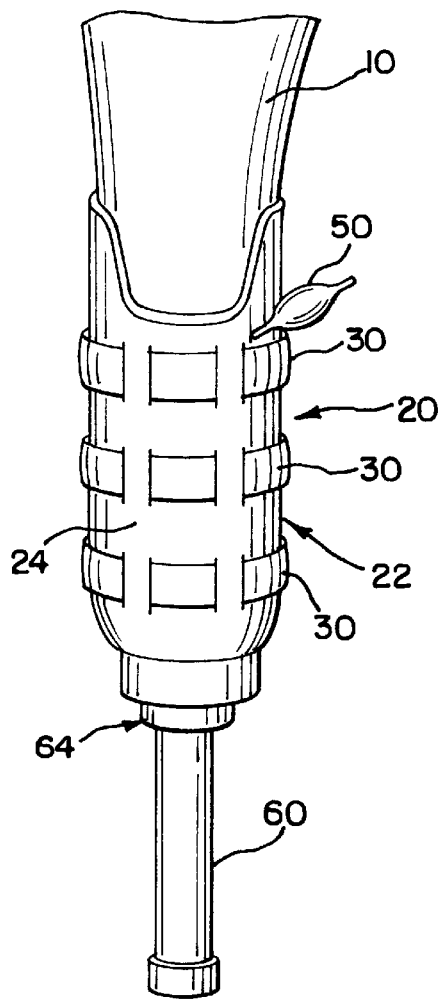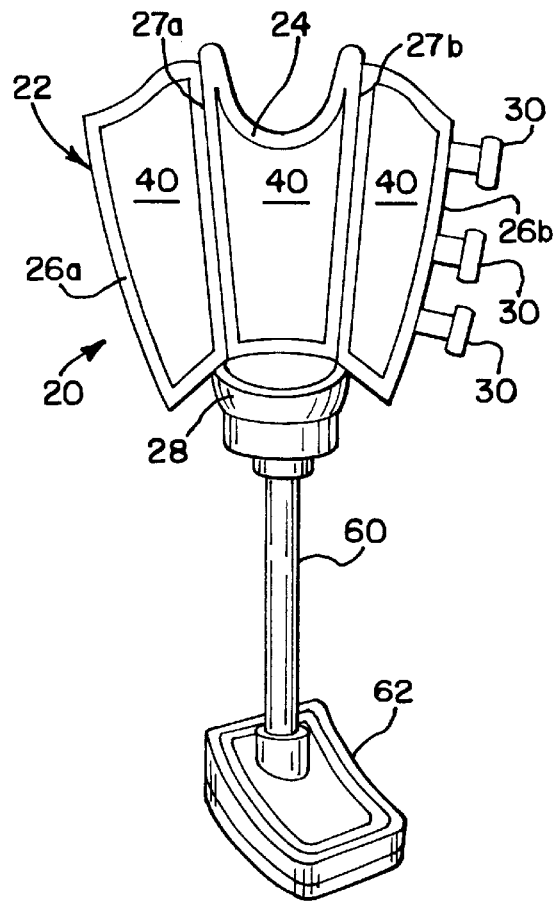

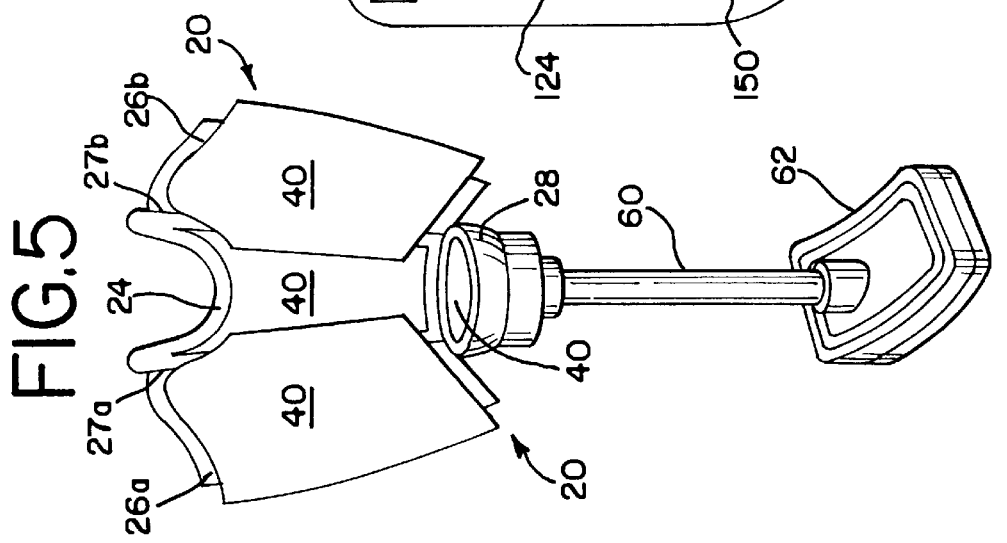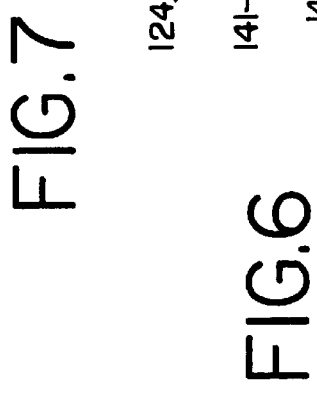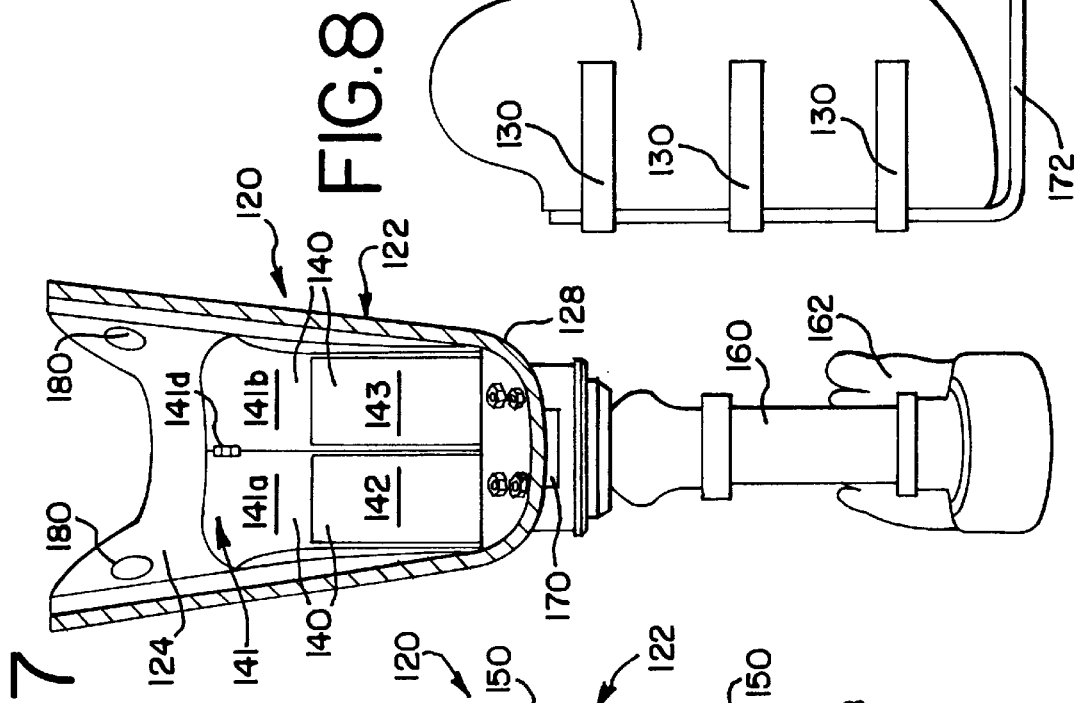

THERAPEUTIC DEVICE FOR AMPUTEES

BACKGROUND OF THE INVENTION

This invention is directed to a therapeutic device for the use in treating people who have undergone surgical removal of a limb by applying the device to the amputee's residual limb. In particular, the invention is directed to a therapeutic device intended for use in the immediate post-operative phase, i.e., immediately after surgical amputation of a limb. More specifically, the invention is directed to a therapeutic prosthesis intended to reduce edema and pain and to promote healing and proper residual limb formation after surgery, while providing support for partial weight-bearing and prosthetic gait training by the amputee and being adjustable to fit a wide range of sizes of residual limbs.

Early fitting of a prosthesis is critical to an amputee's successful rehabilitation. It is very important for the amputee to resume physical activity as soon as possible, after amputation both for physical as well as psychological reasons and because the application of compression to the residual limb is beneficial to the healing process. The early use of a prosthesis helps the amputee quickly re-establish a bilateral body image and accept the use of a prosthetic device. The use of a prosthetic device soon after amputation surgery prevents muscle contractures and loss of muscle strength in the amputee, protects the residual limb from trauma, and helps the amputee develop a tolerance to weight bearing and to learn to balance on a prosthesis. Overall, early use of a post-operative prosthesis reduces complications and the length of the hospital stay for the amputee, and speeds up the training and adjustment period for the new prosthetic device user.

While the residual limb heals after surgery, the amputee cannot be immediately fitted with a rigid socket permanent prosthesis because of wound healing issues, swelling and the need for dressing. Following surgery, the residual limb undergoes dramatic changes in size and shape. To accommodate these changes, various preparatory or interim prostheses are employed as a temporary measure prior to a permanent fitting. A new amputee typically goes through several stages of prosthetic devices while the residual limb is healing and maturing to a stable shape and size. The amputee is eventually provided with a permanent prosthesis, usually a custom-molded socket attached to a metal pylon with a foot. A permanent prosthesis is used on a continuing basis until the device wears out or the amputee experiences changes to the residual limb.

In the immediate post-surgical stage, i.e., during the first several weeks after surgery, amputees may be provided with a rigid dressing, such as a plaster of Paris socket or an initial post-operative prosthesis ("IPOP."), to protect and mold the residual limb. These dressings, however, have limited usefulness because they are non-removable and non-adjustable.

As a more common alternative, to enhance shrinkage and permit access to the surgical wound, elastic bandages and wraps are sometimes used. However, use of such bandaging may lead to skin breakdown and distal edema, and does not protect against developing a contracture or wound trauma. To avoid these complications, a removable rigid dressing can be used. Such prior art removable rigid dressings ("RRD") are described more fully in an article entitled "Removable Rigid Dressing for Below-knee Amputees,"by Yeongchi Wu and Harold Krick, appearing in *Clinical Prosthetics and Orthotics*, Vol. 11, No. 1, pp. 33–44 (1987).

The authors of that prior art article state that their removable rigid system reduces pain, prevents residual limb trauma, promotes soft tissue immobilization to facilitate wound healing, fosters rapid maturation of the residual limb, leads to more rapid shrinkage, and provides effective edema control. They further clam that with a removable rigid post-operative dressing, there is less change in residual limb volume once the amputee is ready for a preparatory or interim prosthesis, thus, there is less need for costly socket changes.

While such rigid dressings of the prior art have been beneficial, they also have certain disadvantages. In particular, these systems are not easily adjustable in response to changes in the size and shape of the residual limb. Also, the device must be removed from the residual limb to make adjustments to these prior art systems. To adjust the fit or prior art systems, socks may be added or removed, but only slight adjustments are possible with this technique. Moreover, prior art RRD systems do not act as prostheses, so immediate psychological benefits to the amputee are not achieved. Since the RRD device can only be donned from the open end it does not effectively provide compression over the entire residual limb if the limb has the common bulbous shape of most new amputations.

It is an object of the present invention to provide a new system for post-operative treatment of a residual limb of an amputee. More specifically, it is an object of the present invention to provide a therapeutic prosthetic device for immediate post-surgical use that reduces edema and pain, protects the residual limb of an amputee from trauma, is easily fitted about the residual limb, allows for easy access to the residual limb so that medical personnel will be able to easily check the wound, and promotes healing and proper residual limb formation after surgery.

It is a further object of the present invention to provide a therapeutic device for the residual limb of an amputee that uses an external adjustable shell and internal adjustable bladders to fine tune adjustments in pressure to the residual limb without removing the shell or undoing the system. Such a system would easily accommodate changes in the size and shape of the residual limb and also allow for the use of bulky dressings. Such a system could also be used with an attachable pylon and foot to promote symmetrical body image and the psychological well-being of the amputee, and will also permit early partial weight bearing.

It is a still further object of the present invention to provide a method for treating a residual limb of an amputee in the post-operative stage to reduce edema and pain, and to promote proper healing and formation of the residual limb. Other objects, advantages, and novel features of the instant invention will be readily apparent to those of skill in the art from the following drawings and detailed description.

SUMMARY OF THE INVENTION

The present invention is directed to a therapeutic device for post-operative treatment of a residual limb of an amputee. The therapeutic device comprises a shell into which the associated residual limb is placed. The shell has a first shell portion and a second shell portion consisting of two overlapping parts. The second shell portion is movable between a position wherein the shell is closed and the residual limb is enveloped therein and a position wherein the shell is open and the residual limb is thereby exposed. A fastening means may be provided for securing the second shell portion to the first shell portion. This fastening means may secure the second shell portion in its first position wherein the shell is closed.

The second shell portion may include a first movable section and a second movable section. Each of these sections may be attached along a respective longitudinal edge thereof to the first shell portion, and they may be pivotable about their respective longitudinal edges. In another embodiment of the invention, the first shell portion includes a receiving means and the second shell portion includes an extension means. In this embodiment, the extension means of the second shell portion is received in the receiving means of the first shell portion when the second shell portion is moved to a position wherein the shell is closed and the residual limb of the amputee is enveloped therein.

The shell may further include a third shell portion adapted to receive the distal end of the residual limb. This third shell portion may be disposed adjacent to the first and second shell portions. A fourth piece may be inserted posteriorly of the shell running up the back of the thigh to prevent knee flexion.

A plurality of inflatable bladders are disposed within the shell. These inflatable bladders may be secured to and extend along the inner surfaces of the first and second shell portions. If the second shell portion includes first and second movable sections, the inflatable bladders may be secured to and extend along the inner surfaces of these movable sections and along the inner surface of the first shell portion. If the shell is provided with a third shell portion, one or more inflatable bladders may likewise be secured to and extend along the inner surface thereof.

Adjacent surfaces of at least two of the inflatable bladders may overlap, and a pump means may be provided for inflating and deflating the bladders. In this regard, a separate fluid pump supply may be provided for independently inflating and deflating each of the inflatable bladders. The combination of the rigid but adjustable shell and inflatable bladders awards the requirement of certain molding of the device as will be noted, facilitating healing.

The present invention is also directed to a method of treating a residual limb of an amputee in the post-operative stage to reduce edema and pain, and to promote proper healing an formation of the residual limb. In the method of the present invention, a therapeutic device having a shell and a plurality of inflatable bladders disposed along the inner surface thereof is provided. The shell of the therapeutic device is opened and the residual limb is placed therein. The shell is closed about the residual limb and therapeutic pneumatic pressure is applied to the residual limb through the plurality of inflatable bladders in cooperation with the shell. This therapeutic pneumatic pressure may be applied by inflating at least one of the plurality of inflatable bladders, and the pressure may be varied and measured in response to the change in shape of the residual limb during the healing process. The therapeutic pneumatic pressure can be adjusted by inflating or deflating at least one of the plurality of inflatable bladders.

After therapeutic pneumatic pressure has been applied to the residual limb, the shell may be opened and the residual limb examined. The shell may then be closed about the residual limb and therapeutic pneumatic pressure re-applied to the residual limb through the plurality of inflatable bladders in cooperation with the shell. Again, the therapeutic pressure may be applied by inflating at least one of the plurality of inflatable bladders.

BRIEF DESCRIPTION OF THE DRAWINGS

The novel features of the invention are set out with particularity in the appended claims, but the invention will be understood more fully and clearly from the following detailed description of the invention as set forth below and in the accompanying drawings, in which:

FIG. 1 is a front elevational view of a residual limb of a below-the-knee amputee;

FIG. 2 is a front elevational view of the residual limb of FIG. 1 placed within a post-operative therapeutic device constructed in accordance with the present invention;

FIG. 3 is a rear elevational view of the residual limb of FIG. 1 placed within a post-operative therapeutic device constructed in accordance with the present invention;

FIG. 4 is a front elevational view of one embodiment of a post-operative therapeutic device constructed in accordance with the present invention;

FIG. 5 is a front elevational view of an alternative embodiment of a post-operative therapeutic device constructed in accordance with the present invention;

FIG. 6 is a front elevational view of a part of a further alternative embodiment of a post-operative therapeutic device constructed in accordance with the present invention;

FIG. 7 is a rear elevational view of the part of the further alternative embodiment of the present invention shown in FIG. 6;

FIG. 8 is a side elevational view of another part of the further alternative embodiment of the present invention shown in FIGS. 6 and 7;

DETAILED DESCRIPTION OF THE INVENTION

Figure 10:
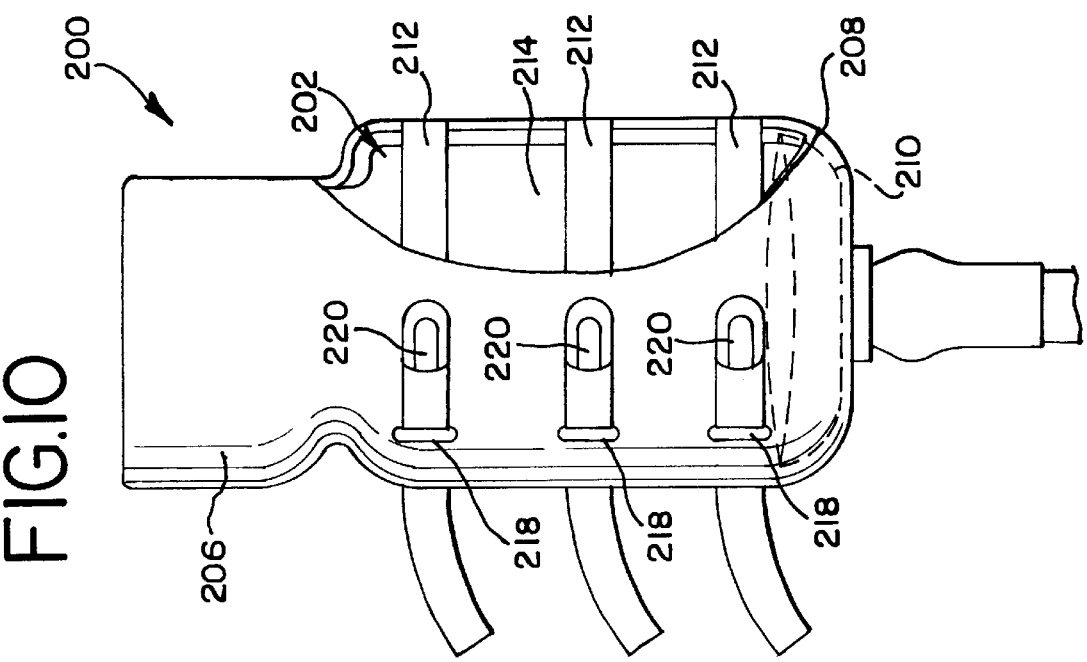
FIG. 10 is a left side elevational view of the device of FIG. 9.

In the following detailed description, the present invention will be described with reference to post-operative therapeutic treatment of the residual limb of a below-the-knee (transtibial) amputee. It should be understood, however, that the invention is not so limited, and may be utilized in the post-operative treatment of other residual limbs (e.g., lower limb: partial foot, ankle disarticulation, transfermoral, etc.; upper limb: partial hand, wrist disarticulation, transradial, transhumeral) by varying the configurations of the shell and bladder shapes.

A residual limb 10 of a below-the-knee amputee (transibial) is shown in FIG. 1. A first embodiment of a therapeutic device 20 for post-operative treatment of this residual limb 10 is shown in FIGS. 2–5. The therapeutic device 20 comprises a shell 22 into which the residual limb 10 is placed. This shell 22 may be made from any suitable rigid or semi-rigid material known to those in the art, e.g., polypropylene or polyethylene and formed by any means known to those in the art, e.g., injection molded or vacuum formed.

The shell 22 has a first shell portion 24 and a second shell portion 26. The second shell portion 26 is movable between a first position wherein the shell 22 is closed and the residual limb 10 is enveloped therein (as shown in FIGS. 2 and 3) and a second position wherein the shell 22 is open and the residual limb 10 is thereby exposed (as shown in FIGS. 4 and 5). Because of the clam-shell-like configuration of the shell 22, the surgically-dressed post-operative residual limb 10 may be inserted safely and carefully into the therapeutic device 20. The shell 22 is designed to open and close about the residual limb 10, thereby making it easy to put on and take off. Moreover, medical personnel will be able to easily check the post-operative wound site and there will be no need for multiple rigid dressings.

A fastening means 30 may be provided for securing the second shell portion 26 to the first shell portion 24. More specifically, the fastening means 30 may secure the second shell portion 26 in a first position wherein the shell 22 is closed. The fastening means 30 may thereafter be undone to allow the shell 22 to be opened and the residual limb 10 examined. In one embodiment of the invention, the fastening means 30 may comprise a plurality of elongated, circumferentially-extending, flexible fastening straps as shown in FIGS. 2, 3 and 4. These Straps can be fabricated with a layer of hook-and-loop fastening material (e.g., VEKCRO®) disposed thereon, such that each strap can be wrapped circumferentially around the shell 22 and attached snugly to itself. An alternative fastening method may employ the use of straps and buckles (as schematically illustrated) if desired.

The second shell portion 26 itself may include a first movable section 26a, and a second movable section 26b as shown in FIGS. 4 and 5. Each of these movable sections 26a, 26b may be pivotably attached along a respective longitudinal edge 27a, 27b to the first shell portion 24, such as, for example, be a hinged connection. The first and second movable sections 26a, 26b may thus be pivoted about their respective longitudinal edges 27a,27b to thereby open and close the shell 22 about the residual limb 10.

As best shown in FIGS. 4 and 5, the shell 22 includes a third shell portion 28 adapted to receive the distal end 12 of the residual limb 10. This third shell portion 28 is disposed adjacent to the first and second shell portions 24, 26. The third shell portion 28 may be integrally formed with either the first shell portion 24 or the second shell portion 26 or may be separately formed and suitably secured to either of the first or second shell portions 24, 26.

A plurality of inflatable bladders 40 are removably disposed within the shell. In general, each bladder 40 comprises a pair of similarly sized, opposed, thin sheets of pliable material (e.g., vinyl plastic) bonded together along their confronting peripheries using known joining techniques such as heat or electronic bonding, for example.

The inflatable bladders 40 are preferably secured to and extend along the inner surfaces of the first and second shell portions 24, 26. If the second shell portion 26 includes movable sections 26a, 26b, bladders 40 may be secured to and extend along the inner surfaces of these sections 26a, 26b as well as along the inner surface of the first shell portion 24. Likewise, if the shell 22 is provided with a third shell portion 28, one or more inflatable bladders 40 may be secured to and extend along the inner surface thereof as shown in FIG. 5. In the embodiment shown, there are three (FIG. 4) or four (FIG. 5) separate inflatable and deflatable bladders 40. In some cases, however, and with some amputees, it may be desirable to have more or fewer bladders 40. The bladders may be removably and adjustably attached to the shell walls by use of hook and loop fasteners (not shown). This technique for holding is illustrated, for example, in U.S. Pat. No. 5,125,400. Alternatively, two way tape may be used.

Notably, because of its unique configuration, the therapeutic device 20 of the present invention need not be custom molded to a particular user, but rather may be used to fit amputees of varying sizes. Once the residual limb 10 is placed within the shell 22 and the second shell portion 26 moved to envelop the limb 10, the fastening means 30 may be adjusted as needed to secure the shell 22 in a closed position about the circumference of the limb. The bladders 40 may then be suitably inflated to essentially encompass the entire circumferential surface of the residual limb 10 and provide a comfortable, soft interface.

In the embodiment of the invention shown in FIG. 5, adjacent surfaces of at least two of the inflatable bladders 40 overlap. When the bladders are spaced apart, there is the potential for swelling of the limb 10 in those regions or "windows" between the bladders where no pressure is applied. Overlapping of the bladders 40 will prevent such "window edema" from developing in the residual limb 10.

In their preferred form, the bladders 40 are filled with air, but other suitable materials may also be used (e.g., liquid, gel, etc.). For example, an inflated bladder filled with styrofoam pellets may be disposed along the interior surface of the third shell portion 28. Such a bladder will contour around the distal end 12 of the residual limb 10 and when deflated will become rigid. One or more of the bladders may also contain a passive reinflation means such as a piece of flexible foam, as described in commonly-assigned U.S. Pat. No. 5,577,998, the disclosure of which is hereby incorporated by reference.

A pump means 50 may be provided for inflating and deflating the bladders 40. In this regard, a separate hand pump may be provided for independently inflating and deflating each bladder 40. These hand pumps are of well-known construction, having a resilient rubber-like squeeze bulb. The squeeze bulb has a nozzle at one end and a one-way valve at the other end. Each bladder 40 may thus be inflated or deflated to achieve the desired pressure against the adjacent portion of the residual limb 10. A pressure gauge may be associated with the pump if desired.

The bladders 40 and shell 22 cooperate to apply pressure to the residual limb 10 that is beneficial to the healing process. In this regard, the bladders 40 and shell 22 help to reduce edema and wound complications, lessen the amputee's pain, and promote healing and proper residual limb formation after surgery. The bladders 40 are adjustable to facilitate conformation of the inner surface of the inventive device to the irregular configuration of the residual limb 10, particularly as the amputee's limb 10 shrinks or swells in the immediate post-operative phase. Because the bladders 40 are independently inflatable or deflatable, they can provide controlled shaping of the residual limb 10 by varying the pressure on selected parts of the limb 10. A compression stocking (not shown) may also be utilized in conjunction with the instant invention to provide additional positive pressure to the affected area of the residual limb 10.

To enable the amputee to resume physical activity shortly after surgery, a prosthetic support or pylon 60 with adjustable components allowing for flexion, extension abduction and rotation of the sock relative to the foot may also extend from the shell 22. This support 60 may be affixed to a prosthetic foot 62 as desired. An adjustment screw device 64 (FIG. 3) may be provided for conveniently adjusting the length of the support 60. The use of the therapeutic device 20 of the present invention in conjunction with a pylon 60 and foot 62 immediately after surgery helps the amputee develop balance and a tolerance to weight bearing and prevents contractures and loss of muscle strength. Also, the application of pressure to the residual limb 10, both pneumatically by the instant invention and by the amputee's weight-bearing activity facilitated by the inventive prosthetic device, promotes the healing process, and the early use of a post-operative prosthesis helps the amputee quickly re-establish a bilateral body image and accept the use of a prosthetic device.

A second embodiment of a therapeutic device 120 constructed in accordance with this invention is illustrated in FIGS. 6–8. This embodiment of the inventive therapeutic device 120 is an improvement of a two-piece prior art initial post-operative prosthesis, such as a known device sold by Flo-tech Orthotic & Prosthetic Systems, Inc. of Geneva, N.Y. as disclosed in U.S. Pat. No. 5,728,165 and U.S. Pat. No. 5,517,209. The device 120 comprises a shell 122 into which the residual limb 10 is placed. The shell 122 may again be formed from any suitable rigid or semi-rigid material known to those in the art, e.g., plastic.

The shell 122 has a first shell portion 124 and a second shell portion 126. the second shell portion 126 is movable between a first position wherein the shell 122 is closed and the residual limb 10 is enveloped therein and a second position wherein the shell 122 is open and at least a portion of the residual limb 10 is thereby exposed.

Unlike the clam type device of the first embodiment, the second shell portion 126 is designed to interfit with the first shell portion 124 and thereby close about the residual limb 10. In this regard, the first shell portion 124 may be provided with a receiving means 170 such as a slot as shown in FIG. 7, and the second shell portion 126 may be provided with a mating extension means 172 such as a tab. To move the second shell portion 126 into a position whereby the shell 122 is closed about the residual limb 10, the extension means 172 of the second shell portion 126 is mated with the receiving means 170 in the first shell portion 124. Conversely, to move the second shell portion 126 to a position whereby the shell 122 is open and at least a portion of the residual limb 10 is exposed, the extension means 172 of the second shell portion 126 is disengaged from the receiving means 170 in the first shell portion 124.

A fastening means 130 may be provided for further securing the second shell portion 126 to the first shell portion 124. More specifically, the fastening means 130 may secure the second shell portion 126 in a first position wherein the shell 122 is closed. The fastening means 130 may thereafter be undone and the extension tab 172 of the second shell portion 126 removed from the slot 170 in the first shell portion 124, thus allowing the shell 122 to be opened and the residual limb 10 examined. In one embodiment of the invention, the fastening means 130 may comprise a plurality of elongated, circumferentially-extending, flexible fastening straps as shown in FIGS. 6 and 8. These straps may be disposed on either one or both of the first and second shell portions 124, 126, and can be fabricated with a layer of hook-and-loop fastening material (e.g., VELCRO®) disposed thereon. The straps can be wrapped about the shell 122 and can be attached snugly to suitable receiving areas of hook-and-loop fastening material disposed on either one or both of the first and second shell portions 124, 126 or by other convenient means.

The shell 122 includes a third shell portion 128 adapted to receive the distal end 12 of the residual limb 10. This third shell portion 128 is disposed adjacent to the first and second shell portions 124, 126. The third shell portion 128 may be integrally formed with either the first shell portion 124 or the second shell portion 126 or may be separately, formed and suitably secured to either of the first or second shell portions 124, 126.

A plurality of inflatable bladders 140 are disposed within the shell 122. In general, each bladder 140 comprises a pair of similarly sized, opposed, thin sheets of pliable material (e.g., vinyl plastic) bonded together along their confronting peripheries using known joining techniques such as heat or electronic bonding, for example. Additional cushioning material 180, such as a soft foam material, may be provided for the residual limb 10 along the inner surfaces of the first and second shell portions 124, 126. In this embodiment, the inflatable bladders 140 are preferably secured to and extend along the inner surfaces of the first shell portion 124 or the second shell portion 126. As shown in FIG. 7, three separate inflatable and deflatable bladders may be provided along the inner surface of the first shell portion 124. In some cases, however, and with some amputees, it may be desirable to have more or fewer bladders 140.

With the configuration shown in FIG. 7, a first bladder 141 extends vertically along the length of the first shell portion 124. This bladder 141 may be formed with two sections 141a, 141b joined together along a common seam 141c; a means 141d for allowing fluid communications between these sections 141a, 141b may also be provided. Two additional bladders 142, 143 are placed in an overlapping configuration with the first bladder 141 along the lower end of the first shell portion 124. In this manner, precise therapeutic pressure may be provided to the distal end of the residual limb 10 by application of controlled pneumatic pressure to any one of the bladders 141, 142, 143. Greater pressure may thus be provided in the lower area of the residual limb 10 nearer the distal end 12 than in the upper areas further from the distal end 12. When the amputee engages in active weight-bearing activities, this pressure configuration encourages positive circulatory blood flow in the residual limb 10.

In their preferred form, the bladders 140 are filled with air, but other suitable materials may also be used (e.g., liquid, gel, etc.). One or more of the bladders 140 may also contain a passive reinflation means such as a piece of flexible foam, as described in commonly-assigned U.S. Pat. No. 5,577,998, the disclosure of which is hereby incorporated by reference.

A pump means 150 may be provided for inflating and deflating the bladders 140. In this regard, a separate hand pump of well-known construction may be provided for independently inflating and deflating each bladder 140. Each bladder 140 may thus be inflated or deflated to achieve the desired pressure against the adjacent portion of the residual limb 10.

The bladders 140 and the shell 122 cooperate to apply pressure to the residual limb 10 that is beneficial to the healing process. In this regard, the bladders 140 and shell 122 help to reduce edema and wound complications, lessen the amputee's pain, and promote healing and proper residual limb formation after surgery. The bladders 140 are adjustable to facilitate conformation of the inner surface of the invention device to the irregular configuration of the residual limb 10, particularly as the amputee'limb 10 shrinks or swells in the immediate post-operative phase. Because the bladders 140 are independently inflatable or deflatable, they can provide controlled shaping of the residual limb 10 by varying the pressure on selected parts of the limb 10.

To enable the amputee to resume physical activity shortly after surgery, a prosthetic support or pylon 160 with adjustable components allowing for flexion, extension, adductions, abduction and rotation of the socket relative to the foot, may also extend from the shell 122. This support 160 may be affixed to a prosthetic foot 162 as desired and adjusted to desired length. The use of the therapeutic device 120 of the present invention in conjunction with a pylon 160 and foot 162 immediately after surgery helps the amputee develop balance and a tolerance to weight bearing and prevents contractures and loss of muscle strength. Also, the application of pressure to the residual limb 10, both pneumatically by the instant invention and by the amputee's weight-bearing activity facilitated by the inventive prosthetic device, promotes the healing process, and the early use of a post-operative prosthesis helps the amputee quickly re-establish a bilateral body image and accept the use of a prosthetic device.

Figure 9:
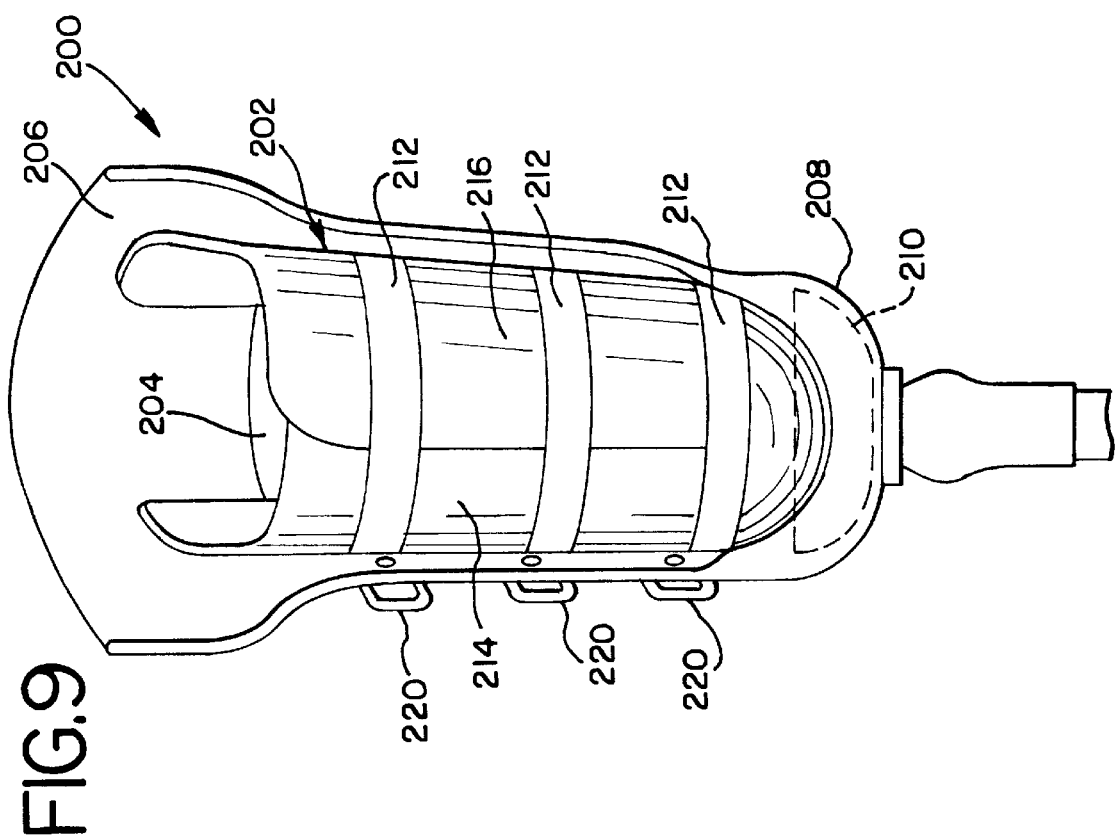
FIG. 9 is a rear elevational view of another embodiment of a post-operative therapeutic device constructed in accordance with the present invention.

A third and preferred alternative configuration of a therapeutic device constructed in accordance with the invention is illustrated in FIGS. 9 and 10 is designated generally by the reference numeral 200. This device 200 comprises an inner shell 202 preferably injection molded from a suitable polypropylene or polyethylene material. Fitted within the inner shell 202 is a connected series of inflatable bladders 204, only a portion of which can be seen, which are held to the inner shell 202 preferably by hook and loop fastening means. Surrounding the inner shell 202 is a rigid shell 206 also constructed of polypropylene or polyethylene. The shell 206 is open at its top and has a cup-shaped bottom portion 208. Fitted within the bottom portion is a pad 210 which may be formed from a suitable closed-cell foam material for cushioning the distal end of the residual limb 10.

The inner shell 202 is relatively rigid. However, it is sufficiently flexible that it can be tightened about the residual limb 10 with the aid of straps 212 that serve to contract the diameter of the inner shell 202 by means of overlapping flap portions 214 and 216. The straps 212 extend around the inner shell 202 and pass through slots 218 in shell 206 whereupon they may be tightened securely by suitable releasable buckles 220. Preferably, the inner shell 202 is fastened at its forward side to the outer shell 206 such as by rivets (not shown). A particular advantage of this devise 200 is that it is highly adjustable to different sizes of residual limbs 10 due to the relative flexibility of the inner shell 202 and the relative rigidity of the outer shell.

The present invention is also directed to a method of treating a residual limb 10 of an amputee in the post-operative stage to promote proper healing and formation of the residual limb. The method of the present invention utilizes the therapeutic devices 20, 120 or 200 described herein. As discussed above, the device 20, 120 or 200 has a shell 22, 122 or 202 and a plurality of inflatable bladders 40, 140 or 204 disposed along the inner surface therof. The shell 22, 122 or 202 is opened and the residual limb 10 is placed therein. The shell 22, 122 or 202 is closed about the residual limb 10 and therapeutic pneumatic pressure is applied to the residual limb 10 through cooperation of the shell 22, 122 or 202 and the plurality of inflatable bladders 40, 140 or 204 about the residual limb 10. This therapeutic pressure may be applied by inflating at least one of the plurality of inflatable bladders 40, 140 or 204. For example, therapeutic pressure of about 10–35 mmHg may be applied while the patient is at rest. This therapeutic pressure may be increased to 50–75 mmHg when the patient begins walking or other weight-bearing activity with the inventive therapeutic device.

The therapeutic pneumatic pressure provided by the respective therapeutic device 20, 120 or 200 may be varied in response to the change in shape of the residual limb 10 during the healing process. Varying of the therapeutic pneumatic pressure may be accomplished by inflating or deflating at least one of the plurality of inflatable bladders 40, 140 or 204. After therapeutic pneumatic pressure has been applied to the residual limb 10 for a period of time, the shell 22, 122 or 202 may be opened and the residual limb 10 examined. In this manner, medical personnel will be able to determine what areas of the residual limb 10 should receive additional pressure from the shell 22, 122, 202 and the bladders 40, 140, 204 and in what areas of the limb 10 the therapeutic pneumatic pressure should be reduced. The respective shell 22, 122 or 202 may then be closed about the residual limb 10 and therapeutic pneumatic pressure re-applied in varying amounts to the desired portions of the residual limb 10 through cooperation of the shell 22, 122, 202 and the plurality of inflatable bladders 40, 140, 204 about the limb 10. Controlled shaping of the residual limb 10 is thus achieved.

The therapeutic devices 20, 120 or 200 of the present invention may also be used in conjunction with a means for producing automatic intermittent compression as described in commonly-assigned U.S. Pat. No. 5,588,955, the disclosure of which is hereby incorporated by reference. Intermittent pneumatic compression is the technique of cyclically compressing the limb with pressure so as to enhance circulation of blood. In place of the pump means 50, 150 described above, the bladders 40, 140 or 204 of the therapeutic devices of the present invention may be connected to a suitable means for producing automatic intermittent compression, such as a pump coupled to a timer and a release valve, to provide the benefits of this technique to the residual limb 10 of an amputee. Desirably, with such a technique, pressure may be transmitted first to the distal portion and then to the proximal portion of the residual limb to provide sequential pressurization to the residual limb. Further, the pressure in the distal portion may be greater than the pressure in the proximal portion to provide advantageous graduated pressurization to the residual limb. These configurations will effectively accelerate the venous flow in the residual limb and thereby decrease edema.

Furthermore, the therapeutic devices 20, 120 or 200 of the present invention may be used in conjunction with cryotherapy techniques, as described in commonly-assigned U.S. Pat. Nos. 5,441,533 and 5,466,250, the disclosures of which are hereby incorporated by reference. For example, rather than utilizing the pump means 50 or 150, the inventive therapeutic devices 20, 120 or 200 may be connected to a system that circulates a chilled fluid between a fluid source of predetermined temperature and the bladders 40, 140 or 204 of the present invention. Therapeutic compression and a low temperature fluid may thus be applied to the residual limb 10 to promote the healing process.

From the foregoing detailed description, it will be evident that there are a number of changes, adaptations and modifications of the present invention which comes within the province of those skilled in the art. However, it is intended that all such variations not departing from the spirit of the invention be considered as within the scope thereof as limited solely by the claims appended hereto.

What is claimed is:

1. A therapeutic device for post-operative treatment of a residual limb of an amputee comprising:

an inner shell having overlapping flap portions;

an outer shell dimensioned and configured to nestingly receive said inner shell with said inner shell being attached thereto;

means for drawing together the overlapping flap portions of said inner shell to reduce the diameter of said inner shell;

a plurality of inflatable bladders disposed completely around an interior wall of said inner shell, said bladders when inflated cooperating with said inner shell to provide therapeutic pneumatic pressure to the entire residual limb of the amputee and promote venous blood flow to the entire residual limb; and a cup portion formed on the bottom of said outer shell to support the distal end of the residual limb of the amputee.

2. The therapeutic device of claim 1 including a pad disposed in said cup portion of said outer shell.

3. The therapeutic device of claim 1 wherein said means for drawing together the overlapping edge portions of said inner shell include a plurality of straps.

4. The therapeutic device of claim 3 wherein said straps wrap around said inner shell and protrude through forward slots formed in said outer shell.

5. The therapeutic device of claim 4 wherein said straps are buckled together outside said outer shell.

6. A therapeutic device for treatment of a residual limb of an amputee comprising:
   a shell, said shell including a first shell portion and a second shell portion, said second shell portion being movable between a first position wherein said shell is closed and the associated residual limb of the amputee is enveloped therein and a second position wherein said shell is open and the residual limb of the amputee is thereby exposed; and
   a series of inflatable chambers disposed completely around an interior wall of said shell, said chambers when inflated cooperating with said shell to provide therapeutic pneumatic pressure to the entire residual limb of the amputee and promote venous blood flow to the entire residual limb; and wherein adjacent surfaces of at least two of said inflatable chambers overlap.

7. The therapeutic device of claim 6 wherein said chambers are formed from independent bladders.

8. The therapeutic device of claim 6 wherein said chambers are formed in a single bladder.

9. The therapeutic device of claim 6 further comprising a pump means for inflating and deflating said series of inflatable chambers.

10. The therapeutic device of claim 9 wherein a separate pump is provided for independently inflating and deflating each of said inflatable chambers.

11. The therapeutic device of claim 6 further comprising a fastening means for securing said second shell portion to said first shell portion.

12. The therapeutic device of claim 11 wherein said fastening means secures said second shell portion in said first position wherein said shell is closed.

13. The therapeutic device of claim 6 further comprising a prosthetic support extending from said shell.

14. The therapeutic device of claim 6 further comprising a means for applying therapeutic intermittent pressure to the residual limb through said series of inflatable chambers.

15. The therapeutic device of claim 6 further comprising a means for applying therapeutic sequential pressure to the residual limb through said series of inflatable chambers.

16. The therapeutic device of claim 15 wherein said means for applying therapeutic sequential pressure applies pressure first to a distal portion and then to a proximal portion of the residual limb.

17. The therapeutic device of claim 6 further comprising a means for applying therapeutic graduated pressure to the residual limb through said series of inflatable chambers.

18. The therapeutic device of claim 17 wherein said means for applying therapeutic graduated pressure applies greater pressure to a distal portion than to a proximal portion of the residual limb.

19. The therapeutic device of claim 6 further comprising a means of applying therapeutic pressure and a chilled fluid to the residual limb thorough said series of inflatable chambers.

* * * * *